United States Patent
Chen et al.

(10) Patent No.: US 9,067,188 B2
(45) Date of Patent: Jun. 30, 2015

(54) SYSTEM AND METHOD FOR CONTINUOUSLY PRODUCING POLYOXYMETHYLENE DIALKYL ETHERS

(71) Applicant: Lanzhou Institute of Chemical Physics, Chinese Academy of Sciences, Lanzhou (CN)

(72) Inventors: Jing Chen, Lanzhou (CN); Heyuan Song, Lanzhou (CN); Chungu Xia, Lanzhou (CN); Meirong Kang, Lanzhou (CN); Ronghua Jin, Lanzhou (CN)

(73) Assignee: Lanzhou Institute of Chemical Physics, Chinese Academy of Sciences, Lanzhou (CN)

( * ) Notice: Subject to any disclaimer, the term of this patent is extended or adjusted under 35 U.S.C. 154(b) by 169 days.

(21) Appl. No.: 13/723,115

(22) Filed: Dec. 20, 2012

(65) Prior Publication Data

US 2014/0114093 A1    Apr. 24, 2014

(30) Foreign Application Priority Data

Oct. 18, 2012  (CN) .......................... 2012 1 0398345

(51) Int. Cl.
| | |
|---|---|
| C07C 41/50 | (2006.01) |
| C07C 41/56 | (2006.01) |
| C07C 41/60 | (2006.01) |
| B01J 19/00 | (2006.01) |
| B01J 19/24 | (2006.01) |
| B01J 14/00 | (2006.01) |
| C07C 41/58 | (2006.01) |

(52) U.S. Cl.
CPC .............. *B01J 14/00* (2013.01); *B01J 19/2465* (2013.01); *B01J 19/00* (2013.01); *C07C 41/60* (2013.01); *C07C 41/56* (2013.01); *C07C 41/50* (2013.01); *C07C 41/58* (2013.01)

(58) Field of Classification Search
None
See application file for complete search history.

(56) References Cited

U.S. PATENT DOCUMENTS

| | | | |
|---|---|---|---|
| 6,534,685 | B1 | 3/2003 | Patrini et al. |
| 7,235,113 | B2 | 6/2007 | Sanfilippo et al. |
| 8,344,183 | B2 | 1/2013 | Chen et al. |
| 2007/0260094 | A1 | 11/2007 | Schelling et al. |
| 2008/0207954 | A1 | 8/2008 | Stroefer et al. |
| 2008/0207955 | A1 | 8/2008 | Stroefer et al. |

(Continued)

FOREIGN PATENT DOCUMENTS

| | | |
|---|---|---|
| CA | 2581502 A1 | 5/2006 |
| CN | 101665414 A | 3/2010 |

(Continued)

*Primary Examiner* — Jennifer A Leung
(74) *Attorney, Agent, or Firm* — Manni Li; Mei & Mark LLP

(57) ABSTRACT

A reaction system and method for producing polyoxymethylene dialkyl ethers ($RO(CH_2O)_nR$, n=1-8) by continuous acetalation of formaldehyde and aliphatic alcohol in the presence of an acid ionic liquid catalyst. The reaction system includes an acetalation reaction unit, a product separation unit, and a catalyst regeneration unit. The recyclable material and catalyst are separated by combining extraction and rectification, and a recovery rate of more than 99% for the catalyst is achieved. Water, as the byproduct, is separated from the reaction system by destroying the azeotrope of water, alcohol, aldehyde, and $RO(CH_2O)_nR$, so that the product separation and catalyst regeneration are facilitated and the catalytic cycle is achieved.

20 Claims, 1 Drawing Sheet

(56) References Cited

U.S. PATENT DOCUMENTS

2011/0288343 A1 11/2011 Chen et al.
2011/0313202 A1 12/2011 Xia et al.
2014/0114092 A1 4/2014 Xia et al.

FOREIGN PATENT DOCUMENTS

| EP | 1505049 A1 | 2/2005 |
| GB | 2483325 A | 3/2012 |
| GB | 2489534 A | 10/2012 |
| WO | WO 2006/045506 A1 | 5/2006 |
| WO | WO 2012/046169 A1 | 4/2012 |

SYSTEM AND METHOD FOR CONTINUOUSLY PRODUCING POLYOXYMETHYLENE DIALKYL ETHERS

CROSS-REFERENCE AND RELATED APPLICATION

This application claims priority on Chinese patent application no. 201210398345.8 filed on Oct. 18, 2012. The contents and subject matter of the priority application is incorporated herein by reference.

FIELD OF THE INVENTION

The invention relates to a novel reaction system and process for continuous production of polyoxymethylene dialkyl ethers, particularly, via continuous acetalation between formaldehyde and an aliphatic alcohol in the presence of an acid ionic liquid catalyst.

BACKGROUND OF THE INVENTION

Polyoxymethylene dialkyl ethers ($RO(CH_2O)_nR$) are novel blending components for clean oil product, which have very high cetane number ($H_3CO(CH_2O)_2CH_3$: 63, $H_3CO(CH_2O)_3CH_3$: 78, $H_3CO(CH_2O)_4CH_3$: 90, $H_3CO(CH_2O)_5CH_3$: 100, $H_5C_2O(CH_2O)_2C_2H_5$: 77, $H_5C_2O(CH_2O)_3C_2H_5$: 89) and oxygen content (methyl series: 42%-49%, ethyl series: 30%-43%). When polyoxymethylene dialkyl ethers are added to the diesel oil at 10%-20%, it significantly improves the combustion characteristic of the diesel oil, increases the thermal efficiency, and greatly reduces the emission of $NO_x$ and soot. Therefore, polyoxymethylene dialkyl ethers are considered as very promising environment-friendly diesel blending components. U.S. Pat. No. 7,235,113 discloses that when 15% of $H_3C(OCH_2)_{3-6}OCH_3$ is added to the diesel oil, the emission of $NO_x$, particles, and hydrocarbon of the exhaust achieves Euro V standard.

EP 1505049 A1 and U.S. Pat. No. 6,534,685 by Snamprogetti S.P.A. Corporation disclose a process for synthesizing polyoxymethylene dimethyl ethers ($DMM_n$) and recycling the materials, where the acetalation reaction between polyformaldehyde and methylal under the catalysis of liquid acid produces $DMM_{2-5}$, the reaction solution is absorbed via silica gel column to remove the liquid acid catalyst, the treated reaction solution enters the rectification column, the light components (trioxymethylene, $DMM_{1-2}$), the products ($DMM_{3-5}$), and the heavy components ($DMM_{\geq 5}$) are separated using two-stage rectification process, and the light components and the heavy components are recycled to the reactor for reuse. PCT Publication WO 2006/045506 A1, Canadian Patent Application Publication CA 2581502 A1, U.S. Patent Application Publication Nos. 20070260094 A1 and 20080207954 A1, by BASF Corporation, disclose similar catalysts and products separation process in which the reaction between trioxymethylene and methanol catalyzed by the liquid acid produces $DMM_{1-10}$ and byproduct water. The reaction solution is subject to the absorption through the packed column charged with the anion exchange resin to remove the acid and water, the treated reaction solution enters the rectification column, and the products $DMM_{3-4}$ are separated through three-stage rectification, where $DMM_n$ with $n \leq 2$ and $n \geq 5$ are recycled to the reactor for reuse. The above reaction solution separation process employs large amount of absorbents, thereby resulting in high energy consumption, and the catalyst cannot be reused.

U.S. Patent Application Publication No. 20080207954 A1 by BASF Corporation discloses a process of producing $DMM_{1-5}$ through the reaction of methanol and formaldehyde in an aqueous solution catalyzed by a liquid acid or a solid acid, where a reaction rectification technique is employed for separating the crude products ($DMM_{1-5}$, raw materials, and water) and the catalyst, and the crude products are separated into the light components ($DMM_{1-2}$ and unreacted raw materials), the products $DMM_{3-4}$ (containing water), and the heavy components $DMM_{>4}$ by a multi-stage rectification process. But in the actual operation of the process, it is difficult to separate methanol and $DMM_{3-4}$ due to the azeotrope of methanol, water, and $DMM_n$. Meanwhile, the good miscibility of methanol, water, and $DMM_{3-4}$ causes phase separation more difficult.

Recently, Lanzhou Institute of Chemical Physics, Chinese Academy of Sciences, in U.S. patent application Ser. No. 13/154,359 and published as U.S. Patent Application Publication No. 20110288343 A1, UK Application No. 1108697.2 and published as GB 2489534A, U.S. patent application Ser. No. 13/164,677 and published as U.S. Patent Application Publication No. 20110313202 A1, and UK Application No. 1110391.8 and published as GB2483325A, discloses a method of synthesizing $DMM_{1-8}$ through the reaction of trioxymethylene and methanol catalyzed by ionic liquids, where the reaction solution is subjected to flash evaporation, film separation, and phase separation to separate the light components ($DMM_{1-2}$, a part of water, unreacted raw material), the crude products $DMM_{3-8}$, and catalyst. In order to achieve the purification of the products $DMM_{3-8}$, small amount of water and catalyst contained in the crude products need to be removed by absorption with silica gel or anion exchange resins, thus, the recovery rate of catalyst of the process is relatively low.

SUMMARY OF THE INVENTION

The invention provides a process for producing polyoxymethylene dialkyl ethers via the continuous acetalation reaction of formaldehyde and aliphatic alcohol by using an acid ionic liquid as a catalyst, where the polyoxymethylene dialkyl ethers are represented by $RO(CH_2O)_nR$ where R is $CH_3$, $CH_2CH_3$, $CH_2CH_2CH_3$, or $CH(CH_3)_2$, and n is an integer ranging from 1 to 8.

In the first aspect, the invention provides a system for continuously producing polyoxymethylene dialkyl ethers (also hereinafter referred to as "the system of the invention"), comprising:

1) an acetalation reaction unit, comprising a single or multi-stage reactor and a heat exchanger, where the reactor is in flow communication with the heat exchanger, and the reaction solution circulates between the reactor and the heat exchanger; wherein an acetalation reaction between the formaldehyde and the aliphatic alcohol is continuously conducted using an acid ionic liquid as a catalyst in the single or multi-stage reactor;

2) a product separation unit, comprising an extraction column and a single or multi-stage rectification column connected to each other in series; wherein a light phase and a heavy phase are extracted from a reactor effluent discharged from the acetalation reaction unit by using an extractant in the product separation unit, wherein the light phase is a product phase containing recyclable materials, the extractant and the products $RO(CH_2O)_{3-8}R$ wherein R is $CH_3$, $CH_2CH_3$, $CH_2CH_2CH_3$, or $CH(CH_3)_2$; and the heavy phase is an aqueous catalyst solution;

3) a catalyst regeneration unit, comprising a film separator; wherein the catalyst regeneration unit receives the heavy phase separated from the product separation unit, and the catalyst in the heavy phase is recycled to the acetalation reaction unit after dehydration.

In one embodiment of the system of the invention, the single or multi-stage reactor is a single or multi-stage tubular reactor or an overflow tank.

In another embodiment of the system of the invention, the rectification columns in the product separation unit include a light components rectification column, an extractant rectification column, and a product rectification column In one embodiment of the system of the invention, the rectification columns used in the system are tray columns or packed columns having a plate number of 3-10.

In one embodiment of the system of the invention, the film separator in the catalyst regeneration unit is selected from a falling film evaporator, a wiped thin film evaporator, or a thin film evaporator.

When the method of the invention is carried out in the system of the invention, the following acid ionic liquids are chosen: the cation moiety of the acid ionic liquids is one selected from a quaternary ammonium cation, a quaternary phosphinium cation, an imidazolium cation, an pyridinium cation, or other heterocyclic cations, and the anion moiety of the acid ionic liquids is one selected from p-toluene sulphonate, trifluoromethyl sulphonate, methyl sulphonate, bisulfatem, or trifluoroacetate.

In a second aspect, the invention provides a method for continuously producing polyoxymethylene dialkyl ethers (hereinafter, is also simply described as "the method of the invention"), comprising the following steps:

1) continuously conducting the acetalation reaction of formaldehyde and aliphatic alcohol at about 100-150° C., about 1.0-5.0 MPa under the protection of nitrogen by using an acid ionic liquid as a catalyst; wherein the resulting reaction effluent contains the produced polyoxymethylene dialkyl ethers and water, as well as the unreacted reaction raw materials and the catalyst;

2) extracting a light phase and a heavy phase from the reaction effluent obtained in step 1) using an extractant, wherein the light phase is a product phase containing the recyclable materials, the extractant and the products $RO(CH_2O)_{3-8}R$ wherein R is $CH_3$, $CH_2CH_3$, $CH_2CH_2CH_3$ or $CH(CH_3)_2$; and the heavy phase is the aqueous catalyst solution;

3) separating most of the water from the aqueous catalyst solution in the heavy phase from step 2) by evaporation, the recovered catalyst is returned to step 1) for reuse.

In the method of the invention, the cation moiety of acid ionic liquids are one selected from a quaternary ammonium cation, a quaternary phosphinium cation, an imidazolium cation, a pyridinium cation, and other heterocyclic cations, while the anion moiety of the acid ionic liquids are one selected from a p-toluene sulphonate, a trifluoromethyl sulphonate, methyl sulphonate, bisulfate and trifluoroacetate.

In one preferred embodiment of the method of the invention, the total amount of the acid ionic liquid catalyst is about 1-5 wt. % of the total reaction materials.

In another preferred embodiment of the method of the invention, the formaldehyde used in step 1) is selected from the aqueous formaldehyde solution, polyformaldehyde, or trioxymethylene. When the aqueous formaldehyde solution is used, the concentration thereof is preferably about 37-90 wt %.

In one preferred embodiment of the method of the invention, the aliphatic alcohol used in step 1) is selected from methanol, ethanol, propanol, or isobutanol, preferably methanol or ethanol.

In another preferred embodiment of the method of the invention, the molar ratio of the formaldehyde to the aliphatic alcohol used in step 1) is about 0.9-3.0.

In one preferred embodiment of the method of the invention, the reaction pressure in step 1) is about 2.0-4.0 Mpa, and the reaction residence time is about 30-60 min In another preferred embodiment of the method of the invention, the extractant used in step 2) is one or more extractant(s) selected from n-hexane, cyclohexane, petroleum ether, chloroform, benzene, toluene, xylene, or ethyl acetate, preferably cyclohexane, benzene, or toluene.

In one preferred embodiment of the method of the invention, the amount of the extractant used in step 2) is 1-3 times more than the volume of the reaction solution. In another preferred embodiment of the method of the invention, the extraction temperature in step 2) is about 25-80° C., preferably about 30-40° C.

In one preferred embodiment of the method of the invention, the evaporating temperature in step 4) is about 20-100° C., preferably about 60-80° C., and the vacuum degree is about from −0.1 MPa to −0.01 MPa, preferably about from −0.05 MPa to −0.02 MPa.

In the system and method of the invention, the recyclable materials separated by rectification in the product separation unit or step 2) specifically include the unreacted reaction raw materials (formaldehyde and aliphatic alcohol), and $RO(CH_2O)_{1-2}R$.

The process parameters and reaction materials such as feedstocks, extractants, and catalysts, used in the method of the invention may also be applied to the system of the invention.

The invention provides the following advantages:

first, the invention employs an extraction separation process, which effectively separates the catalyst and the products, and the recovery rate of the catalyst is 99% or more;

second, the invention effectively separates the byproduct water from the products $RO(CH_2O)_{1-8}R$, as well as the reaction raw materials aliphatic alcohol and formaldehyde, destroys the azeotrope of the water with $RO(CH_2O)_nR$, alcohols, and aldehydes, and thus effectively separates the products; and third, the work up of the catalyst solution is easy, achieving the regeneration and recycling of the catalyst.

Figure 1:
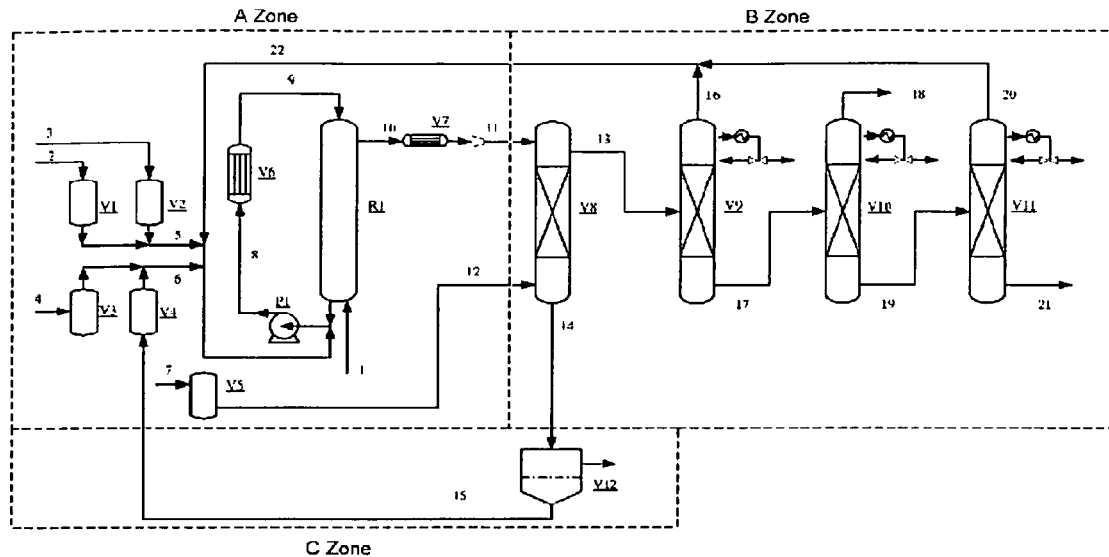
FIG. 1 is a schematic diagram showing the device configuration and process flow in one embodiment of the present invention for continuously producing the polyoxymethylene dialkyl ethers by condensation reaction.

The figures are only used for describing the schematic process flow of the technical solution of the invention, where only the necessary devices for explaining the process are drawn. For simplicity and clarity, the other necessary devices are omitted, such as meters, gas bus devices, pumps, valves, and intermediate tanks, etc.

DETAILED DESCRIPTION OF THE INVENTION

The technical process of the invention is illustrated in association with the devices used in the method of the present invention as follows (hereinafter, A, B, and C zones correspond to the zones noted by the reference signs A, B, and C in FIG. 1, respectively):

A. In the reaction zone A (corresponds to the "acetalation reaction unit" of the system of the invention), with the acid ionic liquid as the catalyst, an acetalation reaction between formaldehyde and aliphatic alcohol are continuously conducted under the protection of nitrogen; the devices configured in the reaction zone may include a single or a multi-stage tubular reactor and a heat exchanger, wherein the reactor is in flow communication with the heat exchanger, and the reaction solution is recycled in the reactor and the heat exchanger.

B. In the product separation zone B (corresponds to the "product separation unit" in the system of the invention), the devices configured in this zone may include an extraction column and a single or a multi-stage rectification column connected to each other in series; the reactor effluent flowed out from the above reaction zone is lowered in pressure, continuously flows into the extraction column where $RO(CH_2O)_{1-8}R$, wherein R is $CH_3$, $CH_2CH_3$, $CH_2CH_2CH_3$, or $CH(CH_3)_2$, and the most of reaction raw materials are extracted by an extractant. The extract liquor continuously flows into the rectification unit, where the recyclable materials, extractant, and products $RO(CH_2O)_{3-8}R$ are separated. The aqueous catalyst solution continuously flows into the catalyst regeneration zone.

C. In the catalyst regeneration zone C (corresponds to the "catalyst regeneration unit" in the system of the invention), a film separator may be provided. The aqueous catalyst solution from the product separation zone is continuously fed into the film separator, where most of the water is separated, and the catalyst continuously flows into the reaction zone for reuse.

The technical process of the method of the invention is specifically described below.

The reaction formula employed in the method of the invention is represented as follows:

$$2\,ROH + n\,CH_2O \xrightarrow{IL} RO(CH_2O)_nR + H_2O$$

wherein:
R in the reaction formula is $CH_3$, $CH_2CH_3$, $CH_2CH_2CH_3$, or $CH(CH_3)_2$, n is an integer ranging from 1 to 8, IL represents an acid ionic liquid catalyst.

As for the acid ionic liquid catalysts used in the invention, it may be chosen with reference to the following preferred examples.

The structure of the examples of the quaternary ammonium cation of the acid ionic liquid catalyst employed in the invention may be:

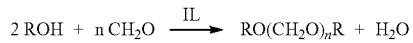

wherein: n and m are integers of 1-15; R, $R_1$, and $R_2$ are linear alkanes having a carbon number of 1-6 or benzene rings; X is $-SO_3H$ or $-COOH$.

The structure of the examples of the quaternary phosphinium cation of the acid ionic liquid catalyst employed in the invention may be:

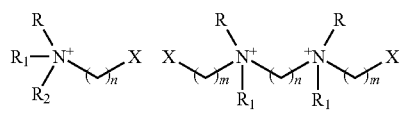

wherein: n and m are integers of 1-15; R, $R_1$, and $R_2$ are linear alkanes having a carbon number of 1-6 or benzene rings; X is $-SO_3H$ or $-COOH$.

The structure of the examples of the imidazolium cation of the acid ionic liquid catalyst employed in the invention may be:

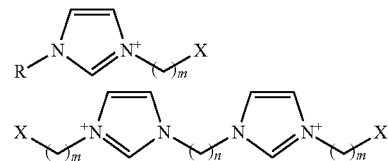

wherein: n and m are integers of 1-15; R is a linear alkane having a carbon number of 1-6 or a benzene ring; X is $-SO_3H$ or $-COOH$.

The structure of the examples of the pyridinium cation of the acid ionic liquid catalyst employed in the invention may be:

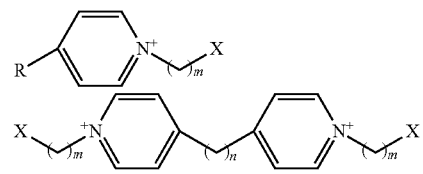

wherein: n and m are integers of 1-15; R is a linear alkane having a carbon number of 1-6 or a benzene ring; X is $-SO_3H$ or $-COOH$.

The structure of the examples of the heterocyclic cation of the acid ionic liquid catalyst employed in the invention may be:

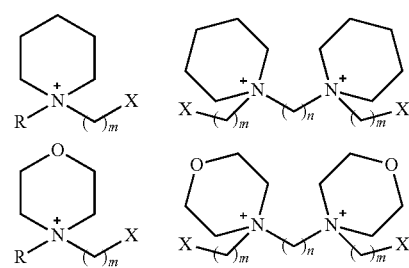

wherein: n and m are integers of 1-15; R is a linear alkane having a carbon number of 1-6 or a benzene ring; X is $-SO_3H$ or $-COOH$.

Examples of the anion of the acid ionic liquid catalyst employed in the invention may include:
$CH_3PhSO_3^-$, $CF_3SO_3^-$, $CH_3SO_3^-$, $HSO_4^-$, $CF_3COO^-$.

It should be noticed here that, unless otherwise specified, all of the pressures used herein represent gauge pressure; furthermore, the description of the following process may relates to devices not shown in the figures, as stated above, these devices are only omitted for the reason of simplicity and ease of describing and illustrating the main configuration of the system of the invention, instead of indicating that these devices are absent or unnecessary. In addition, it should be understood that, the following description and examples are only the preferred embodiments for illustrating the invention, which is not intended to limit the scope of the invention, therefore the devices used in the system of the invention do not only limited to the specific devices mentioned below. Without further elaboration, it is believed that one skilled in the art can choose the suitable devices with the similar function according to the specific situation based on the teaching of the invention.

The process flow of the method of the invention is described below in associated with the specific configuration of the process devices shown in FIG. 1 and the flow direction of the material streams shown in FIG. 2.

(1) When the reaction starts or the catalyst is supplemented, the ionic liquid catalyst is added via pipe-line 4 into a catalyst storage tank V3, and then after fed into a reactor R1 via pump, it is recycled to the whole system.

(2) Acetalation reaction: the whole system is purged with $N_2$, the oxygen content detected by the discharged exhaust gas detecting system is lower than 10 ppm. The reaction raw materials, formaldehyde or trioxymethylene and aliphatic alcohol, are charged into raw material storage tanks V1 and V2 via pipe-line 2 and pipe-line 3, respectively. The reaction raw materials are metered by a liquid mass velocity meter (not shown in the Figures) via pipe-line 5, the light components recycled via pipe-line 22 and the catalyst solution recycled via pipe-line 15, respectively, are metered and continuously flow into the acetalation reactor R1. $N_2$ is cleaned through a cleaning unit, and metered into the reactor R1 via pipe-line 1. The acetalation reaction occurs at certain temperature and pressure. The effluent stream from the bottom of the reactor R1 is transferred through pipe-line 8, by means of pump P1, and into a heat exchanger V6, then returned to the reactor R1 through pipe-line 9. The reactor R1 in flow communication with the heat exchanger V6, and the reaction solution is circulated between the reactor R1 and the heat exchanger V6. The overhead stream from the reactor R1 comprises the catalyst, $RO(CH_2O)_{1-8}R$, water, unreacted aliphatic alcohol and formaldehyde or trioxymethylene.

(3) Extraction separation: the effluent of the reactor R1 is fed into a heat exchanger V7 via pipe-line 10, followed by cooling down and lowering the pressure, it is transferred through pipe-line 11 into an extraction column V8. The extractant is supplied from a storage tank V5 via pipe-line 12, and into the extraction column V8, where the reaction solution is conversely and sufficiently contacted with the extractant. The light phase (product phase) continuously enters a rectification column V9 from the head of the column via pipe-line 13, and the heavy phase (aqueous catalyst solution) continuously enters a film evaporator V12 from the bottom of the column via pipe-line 14.

(4) Rectification separation: the product phase containing $RO(CH_2O)_{1-8}R$, the extractant, unreacted aliphatic alcohol and formaldehyde is rectified in the rectification column V9. The light components continuously distilled from the head of the column (mainly containing formaldehyde, aliphatic alcohol, and $ROCH_2OR$) are returned to the reaction system via pipe-line 16 after cooling down. The bottom liquid is fed into a rectification column V10 via pipe-line 17, and the extractant distilled from the head of the column is returned to the extractant storage tank V5 via pipe-line 18 for reuse; the bottom liquid enters a rectification column V11 via pipe-line 19, $RO(CH_2O)_2R$ and trioxymethylene are distilled from the head of the column via pipe-line 20 and returned to the reaction system for reuse, and the bottom effluent products $RO(CH_2O)_{3-8}R$ enter a product storage tank via pipe-line 21.

(5) Catalyst dehydration: the aqueous catalyst solution is continuously fed from the bottom of the extraction column via pipe-line 14 into a film evaporator V12. Flash distillation is conducted at from about 60 to 80° C./from about −0.05 to −0.02 MPa for dehydrating, and the catalyst is recovered to the catalyst storage tank V4 via pipe-line 15.

Production examples are provided as follows with reference to the configuration of FIG. 1 and the flow direction of the material streams in FIG. 2.

EXAMPLES

The catalysts used in the examples are as follows:

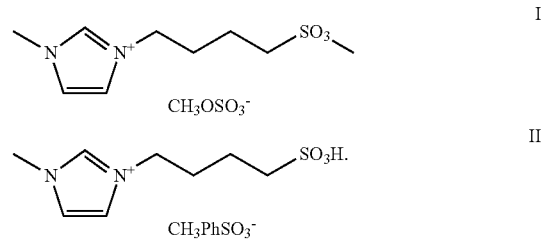

Example 1

Figure 2:
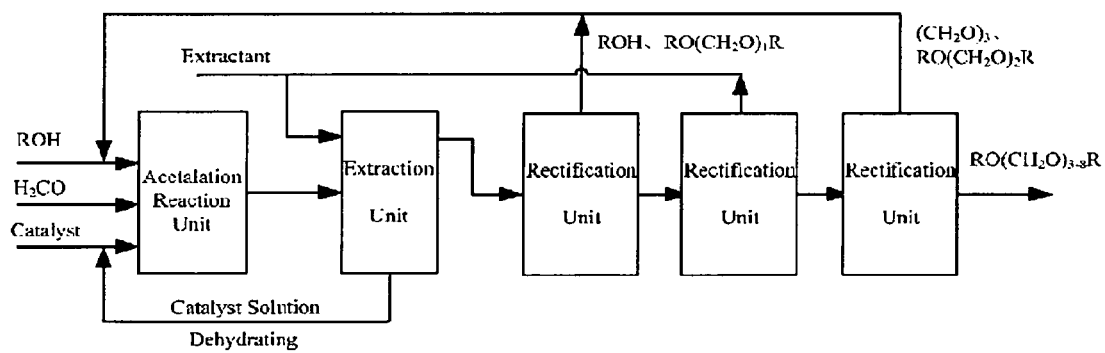
FIG. 2 is a flow chart showing the flow direction of the reaction material streams in one embodiment of the method of the present invention.

In the reaction process shown in FIG. 1, the volume of the reactor R1 is 1000 mL, the reactor R1 is in flow communication with the heat exchanger, and the reaction solution is recycled in the reactor and the heat exchanger.

The system was purged with high-purity nitrogen to replace air. Ionic liquid catalyst I was fed into the fluidized reaction system. The feeding speed was 1.0 g/h. The feeding was stopped until the catalyst begins to be circulated, so that the concentration of the catalyst was ensured to be not less than 4%. Trioxymethylene with a purity of 98.5 wt %, and the methanol with a purity of 99% were charged under the feeding speed of 15.0 mL/h and 100 mL/h, respectively into the reactor R1 to conduct the reaction. The operating condition of the reactor R1 was controlled at 115-120° C. and 2.5-3.5 MPa.

The reaction solution is fed into the extraction column V8, and the feeding speed of the extractant benzene is 25 mL/h The heavy phase (i.e., an aqueous catalyst solution) continuously entered the film evaporator V12 from the bottom of the column, it was dehydrated at 60° C./−0.05 MPa, and the catalyst was fed into the reactor for reuse. The light phase (i.e., the product phase) continuously entered the rectification column V9 from the head of the column Light components comprising $CH_3OCH_2OCH_3$, formaldehyde, and methanol were continuously distilled from the head of the column at 40-60° C., directly returned to the reaction unit A for reuse. The bottoms were fed into the rectification column V10, where the extractant benzene was distilled from the head of the column at 78° C.-80° C. and returned back to the storage tank V5 for reuse; the bottoms entered the rectification column V11, where $CH_3O(CH_2O)_2CH_3$ and trioxymethylene were distilled from the head of the column at 98-110° C. and returned back to the reaction unit for reuse. The products $CH_3O(CH_2O)_{3-8}CH_3$ discharged from the bottom of the column entered the product storage tank. The reaction solution, extraction liquid, aqueous catalyst solution, and products were sampled at regular time and the samples were quantitatively analyzed with a gas chromatograph. The acetalation reaction continues for 100 h. The results of the experiment are shown in Table 1.

TABLE 1

| The pipe-line where the sampling point is | Discharge speed mL/h | Products distribution (%) | | | | | | | | | | | |
|---|---|---|---|---|---|---|---|---|---|---|---|---|---|
| | | benzene | methanol | trioxymethylene | water | \multicolumn{8}{c}{$CH_3O(CH_2O)_nCH_3$ n =} |
| | | | | | | 1 | 2 | 3 | 4 | 5 | 6 | 7 | 8 |
| 11 | 25.8 | 0 | 2.9 | 2.3 | 6.4 | 28.2 | 30.5 | 20.7 | 10.5 | 3.9 | 0.8 | 0.2 | 0 |
| 13 | 47.3 | 45.1 | 1.5 | 1.2 | 0.3 | 15.5 | 16.7 | 11.4 | 5.8 | 2.1 | 0.4 | 0.1 | 0 |
| 14 | 2.7 | 5.8 | 0.2 | 0.1 | 59.0 | 0.2 | 0 | 0 | 0 | 0 | 0 | 0 | 0 |
| 21 | 9.0 | 0 | 0.1 | 0.2 | 0.05 | 0 | 4.2 | 51.3 | 30.0 | 10.7 | 3.0 | 0.5 | 0 |

Note:
the extracted aqueous catalyst solution (14) contains catalyst in 37.0%.

Example 2

The basic process steps and the configuration of the devices were the same as Example 1, except that the ionic liquid II was added as the catalyst, the feeding speed was 0.6 g/h. The feeding was stopped until the catalyst begins to be circulated; the reaction materials were 80 wt % of aqueous formaldehyde solution, and methanol with a purity of 99%, and the feeding speed was 10.8 mL/h and 5.8 mL/h, respectively. The operating condition of the reactor R1 was controlled at 125-130° C., and 3.5-4.0 MPa. The acetalation reaction ran continuously for 100 hours. The results are shown in Table 2.

TABLE 2

| The pipe-line where the sampling point is | Discharge speed mL/h | Products distribution (%) | | | | | | | | | | | |
|---|---|---|---|---|---|---|---|---|---|---|---|---|---|
| | | benzene | methanol | formaldehyde | water | \multicolumn{8}{c}{$CH_3O(CH_2O)_nCH_3$ n=} |
| | | | | | | 1 | 2 | 3 | 4 | 5 | 6 | 7 | 8 |
| 11 | 17.0 | 0 | 2.4 | 5.1 | 19.3 | 29.1 | 26.2 | 11.6 | 3.5 | 1.9 | 0.5 | 0 | 0 |
| 13 | 29.5 | 52.3 | 1.3 | 2.7 | 0.2 | 16.8 | 15.2 | 7.6 | 2.0 | 1.0 | 0.3 | 0 | 0 |
| 14 | 4.5 | 5.4 | 5.5 | 2.0 | 66.7 | 6.7 | 0.4 | 0 | 0 | 0 | 0 | 0 | 0 |
| 21 | 3.0 | 0 | 0.3 | 0 | 0.05 | 0.1 | 1.2 | 59.5 | 26.8 | 9.8 | 2.6 | 0 | 0 |

Note:
the extracted aqueous catalyst solution (14) contains catalyst in 13.3%.

Example 3

The basic process steps and the configuration of the devices as well as the parameters thereof were the same as Example 1, except that toluene was used as the extractant. The reaction ran continuously for 100 hours, resulting in 9.1 mL/h of $DMM_{3-8}$ product (from pipe-line 21).

Example 4

The basic process steps and the configuration of the devices as well as the parameters thereof were the same as Example 1, except that the amount of the extractant was one time more than the volume of the reaction solution. The reaction ran continuously for 100 hours, resulting in 8.8 mL/h of $DMM_{3-8}$ product (from pipe-line 21).

Example 5

The basic process steps and the configuration of the devices as well as the parameters thereof were the same as Example 1, except that the molar ratio of the trioxymethylene to the methanol was 0.5:1. The reaction ran continuously for 100 hours, resulting in 9.2 mL/h of $DMM_{3-8}$ product (from pipe-line 21).

Example 6

The basic process steps and the configuration of the devices as well as the parameters thereof were the same as Example 1, except that the amount of catalyst IL II was 2 wt. % of the total charge amount. The reaction ran continuously for 100 hours, resulting in 7.3 mL/h of $DMM_{3-8}$ product (from pipe-line 21).

We claim:

1. A reaction system for continuously producing polyoxymethylene dialkyl ethers, comprising:

an acetalation reaction unit, comprising a single or multi-stage reactor and a heat exchanger, wherein the reactor is in flow communication with the heat exchanger, and a reaction solution circulates between the reactor and the heat exchanger; an acetalation reaction of formaldehyde and aliphatic alcohol is continuously conducted by using an acid ionic liquid as a catalyst in the reactor;

a product separation unit, comprising an extraction column and a single or multi-stage rectification column connected to each other in series, wherein a light phase and a heavy phase are extracted from a reaction effluent discharged from the acetalation reaction unit by using an extractant in the product separation unit; the light phase is a product phase containing recyclable materials, the extractant, and products $RO(CH_2O)_{3-8}R$ wherein R is $CH_3$, $CH_2CH_3$, $CH_2CH_2CH_3$, or $CH(CH_3)_2$; and the heavy phase is an aqueous catalyst solution; and a catalyst regeneration unit, comprising a film separator, wherein the catalyst regeneration unit receives the heavy phase separated from the product separation unit, and the catalyst in the heavy phase is recycled to the acetalation reaction unit after dehydration in the catalyst regeneration unit.

2. The reaction system of claim 1, wherein the single or multi-stage reactor in the acetalation reaction unit is a single or multi-stage tubular reactor or an overflow tank.

3. The reaction system of claim 1, wherein the single or multi-stage rectification column in the product separation unit includes a light component rectification column, an extractant rectification column and a product rectification column.

4. The reaction system of claim 1, wherein the single or multi-stage rectification column in the product separation unit is a tray column or a packed column having a plate number of 3-10.

5. The reaction system of claim 1, wherein the film separator in the catalyst regeneration unit is selected from a falling film evaporator, a wiped thin film evaporator or a thin film evaporator.

6. A method for producing polyoxymethylene dialkyl ethers in the reaction system according to claim 1, comprising:
  1) continuously conducting the acetalation reaction of the raw materials formaldehyde and the aliphatic alcohol in the acetalation reaction unit at about 100-150° C., and about 1.0-5.0 MPa under the protection of nitrogen by using an acid ionic liquid as a catalyst; wherein the reaction effluent comprises polyoxymethylene dialkyl ethers, water, unreacted raw materials, and the catalyst;
  2) extracting the light phase and the heavy phase from the reaction effluent obtained in step 1) using an extractant, wherein the light phase is the product phase containing the recyclable materials, the extractant, and the products $RO(CH_2O)_{3-8}R$ wherein R is $CH_3$, $CH_2CH_3$, $CH_2CH_2CH_3$, or $CH(CH_3)_2$; and the heavy phase is the aqueous catalyst solution; and
  3) separating most of the water from the aqueous catalyst solution in the heavy phase from step 2) by evaporation, and returning recovered catalyst to step 1) for reuse.

7. The method of claim 6, wherein the total amount of the acid ionic liquid catalyst is about 1-5 wt. % of the raw materials.

8. The method of claim 6, wherein the formaldehyde used in step 1) is an aqueous formaldehyde solution, polyformaldehyde, or trioxymethylene.

9. The method of claim 8, wherein the concentration of the aqueous formaldehyde solution is about 37-90 wt %.

10. The method of claim 6, wherein the aliphatic alcohol used in step 1) is methanol, ethanol, propanol, or isobutanol.

11. The method of claim 6, wherein the molar ratio of the formaldehyde to the aliphatic alcohol used in step 1) is about 0.9 to 3.0.

12. The method of claim 6, wherein the reaction pressure in step 1) is about 2.0 MPa to 4.0 MPa, and the reaction residence time is about 30 to 60 min.

13. The method of claim 6, wherein the extractant used in step 2) is n-hexane, cyclohexane, petroleum ether, chloroform, benzene, toluene, xylene, ethyl acetate, or a mixture thereof.

14. The method of claim 6, wherein the amount of the extractant used in step 2) is 1-3 times more than the volume of the reaction solution.

15. The method of claim 6, wherein the extraction temperature in step 2) is about 25 to 80° C.

16. The method of claim 15, wherein the extraction temperature in step 2) is about 30 to 40° C.

17. The method of claim 6, wherein the evaporating temperature in step 3) is about 20 to 100° C., and the vacuum degree is about from −0.1 MPa to −0.01 MPa.

18. The method of claim 17, wherein the evaporating temperature in step 3) is about 60 to 80° C.

19. The method of claim 17, wherein the vacuum degree is about from −0.05 MPa to −0.02 MPa.

20. The method of claim 6, wherein the acid ionic liquid has a cation moiety that is a quaternary ammonium cation, a quaternary phosphinium cation, an imidazolium cation, a pyridinium cation, or a heterocyclic cation, and the acid ionic liquid has an anion moiety that is a p-toluene sulphonate, a trifluoromethyl sulphonate, methyl sulphonate, bisulfate, or trifluoroacetate.

* * * * *